US00PP09720P

United States Patent [19]

Kordes

[11] Patent Number: Plant 9,720

[45] Date of Patent: Dec. 3, 1996

[54] FLORIBUNDA ROSE PLANT NAMED 'KORPLASINA'

[75] Inventor: Wilhelm Kordes, Sparrieshoop, Germany

[73] Assignee: Bear Creek Gardens, Inc., Medford, Oreg.

[21] Appl. No.: 596,447

[22] Filed: Feb. 2, 1996

[51] Int. Cl.[6] ..... A01H 5/00

[52] U.S. Cl. ..... Plt./23

[58] Field of Search ..... Plt./23, 14

*Primary Examiner*—Howard J. Locker

*Attorney, Agent, or Firm*—Klarquist Sparkman Campbell Leigh & Whinston

[57] ABSTRACT

A new floribunda rose plant having high production of cut flowers, greenish white bud and creamy white open flowers, few thorns, hard petal substance, and long vase life.

1 Drawing Sheet

The present invention relates to a new and distinct variety of rose plant of the floribunda class which was originated by me by crossing an unnamed seedling with the variety KORampa, U.S. Plant Pat. No. 5,411.

The primary objective of this breeding was to produce a new rose variety having the high production, good vase life and hard petals of the pink floribunda female parent combined with the high production and light cream flower (champagne color) of the male parent. The objective was substantially achieved, along with other desirable improvements, as evidenced by the following unique combination of characteristics that are outstanding in the new variety and that distinguish it from its parents, as well as from all other varieties of which I am aware:

1. High production of cut flowers (an average of over 30 blooms per plant per year;
2. Greenish white bud opening to a creamy white flower;
3. Long vase life;
4. Hard petal substance; and
5. Few thorns.

Asexual reproduction of this new variety by budding, as performed at Wasco, Calif., and Sparrieshoop, Germany, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—KORampa.

Classification:

*Botanical.*—*Rosa hybrida.*

*Commercial.*—Floribunda.

FLOWER

Observations made from specimens grown in a greenhouse environment in Somis, Calif., and Sparrieshoop, Germany, January through December, 1995.

Blooming habit: Continuous.

Bud:

*Size.*—1¼ inches long when the petals start to unfurl.

*Form.*—The bud form is short, blunt topped.

*Color.*—When sepals first divide, bud color is Yellow-Green Group 149D. When half blown, the upper sides of the petals are Green-White Group 157D; and the lower sides of the petals are Green-White Group 157D.

*Sepals.*—Color: Green Group 138C. Surface texture: Covered in fine hairs. There are three normally heavily appendaged sepals. There are two unappendaged sepals with hairy edges.

*Receptacle.*—Color: Green Group 143B. Shape: Funnel. Size: Small (¼"×⅜"). Surface: Smooth.

*Peduncle.*—Length: Short (2½"–3"). Surface: Smooth with an occasional small prickle. Color: Medium green. Strength: Stiff, erect and slender.

Bloom:

*Size.*—Medium. Average open size is 3 inches to 3½ inches.

*Borne.*—Singly and several together in large, very open rounded clusters (3 to 5 flowers).

*Stems.*—Medium, strong. Average length is about 18 inches to 22 inches.

*Production.*—High, averaging over 30 blooms per plant per year.

*Form.*—When first open: High center. Permanence: Flattens, all petals curl.

*Petalage.*—Number of petals under normal conditions: 30.

*Color.*—The upper side of the petals is Green-White Group 157D. The reverse side of the petals is Green-White Group 157D. Each petal has a very small (1/16" by 1/16") green color spot at the point of attachment to the petal base. The major color on the upper side is Green-White Group 157D.

*Variegations.*—None.

*Discoloration.*—The general tonality at the end of the first day: No change. At the end of the third day: No change. By day 7 or 8, on the plant the petals shatter. In the vase the flowers will stay viable for 14 to 16 days.

*Fragrance.*—None.

Petals:

*Texture.*—Thick.

*Shape.*—Round.

*Form.*—Tips slightly recurved.

*Arrangement.*—Imbricated, with few petaloids.

*Persistence.*—Drop off cleanly.

*Lastingness.*—On the plant: Very long; 7 to 8 days. As a cut flower: Very long; 14 to 16 days.

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Greenish white.

*Stigmas.*—Color: Greenish white.

Form: Bush.

Growth: Vigorous; upright; branching. After one year in the greenhouse, with constant cutting, the variety is 5 feet tall.

Foliage:

*Number of leaflets on normal mid-stem leaves.*—5.

*Size.*—Medium (5"×3½").

*Quantity.*—Abundant.

*Color.*—New foliage: Moderate anthocyanin. Upper and lower are greyed red 178B. Old foliage: Upper — Green Group 137A. Lower — Green Group 138B.

Leaflets:

*Shape.*—Pointed oval.

*Texture.*—Upper side: Glossy, smooth.

*Edge.*—Serrated.

*Serration.*—Single, small.

*Petiole rachis.*—Color: Green.

*Petiole underside.*—Smooth.

*Stipules.*—Medium (½"), serrated, bearded.

*Disease resistance.*—Resistant to mildew under normal growing conditions at Somis, Calif. Not tested for rust and blackspot as this is a greenhouse cut rose.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Short (1/16"), hooked downward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by high production of cut flowers, greenish white bud and creamy white open flowers, few thorns, hard petal substance, and long vase life.

* * * * *

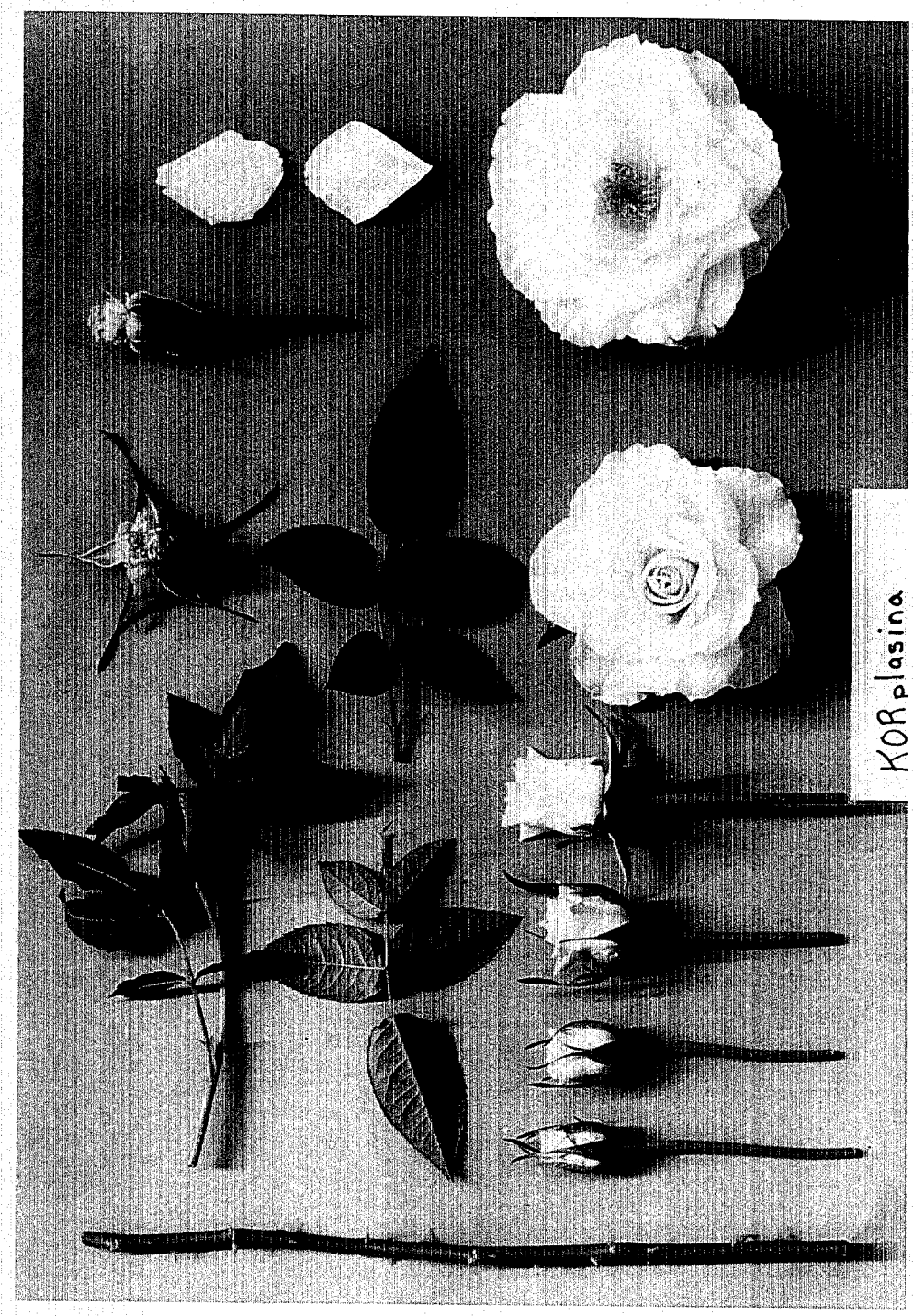
KORplasina